United States Patent [19]

Hulsink

[11] Patent Number: 5,096,416
[45] Date of Patent: Mar. 17, 1992

[54] ORTHODONTIC RETAINER

[75] Inventor: Jan H. Hulsink, Michigan City, Ind.

[73] Assignee: TP Orthodontics, Inc., Westville, Ind.

[21] Appl. No.: 717,164

[22] Filed: Jun. 17, 1991

Related U.S. Application Data

[63] Continuation of Ser. No. 517,370, May 1, 1990, abandoned.

[51] Int. Cl.$^5$ .................................................. A61C 3/00
[52] U.S. Cl. ............................................................. 433/6
[58] Field of Search ........................................ 433/6, 7

[56] References Cited

U.S. PATENT DOCUMENTS

| | | | |
|---|---|---|---|
| 3,849,885 | 11/1974 | Robins | |
| 4,224,021 | 9/1980 | Foxman | 433/2 |
| 4,253,828 | 3/1981 | Coles et al. | 433/6 |
| 4,299,568 | 11/1981 | Crowley | 433/6 |
| 4,516,936 | 5/1985 | Hulsink | 433/6 |

OTHER PUBLICATIONS

TP Catalog 908, 1987, pp. 137–138.
Straight-Talk, vol. 19, No. 4, Jan.-Feb. 1989, p. 4 (TP Orthodontics).

*Primary Examiner*—Cary E. O'Connor
*Attorney, Agent, or Firm*—Lloyd L. Zickert

[57] ABSTRACT

An orthodontic appliance of the type normally referred to as a retainer for retention of teeth moved during a period of orthodontic treatment, wherein the retainer is made of acrylic sections or plates interconnected by resilient wire where at least one posterior lingual section is flexible relative to the anterior section to aid in the fabrication and placement of the appliance.

12 Claims, 3 Drawing Sheets

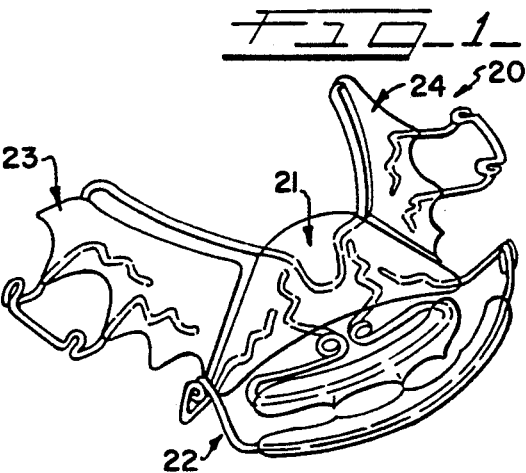
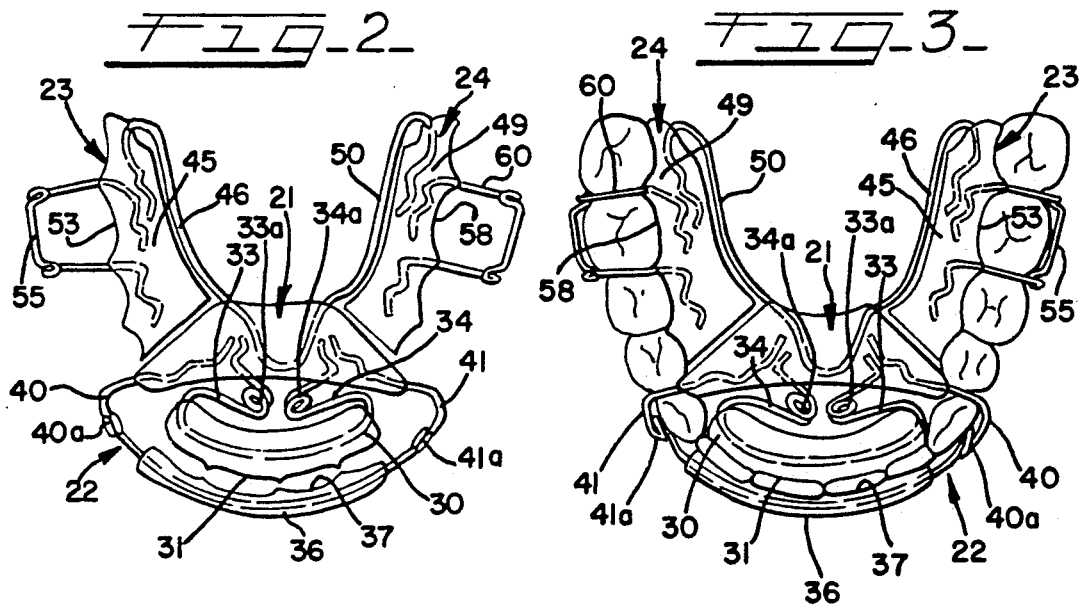
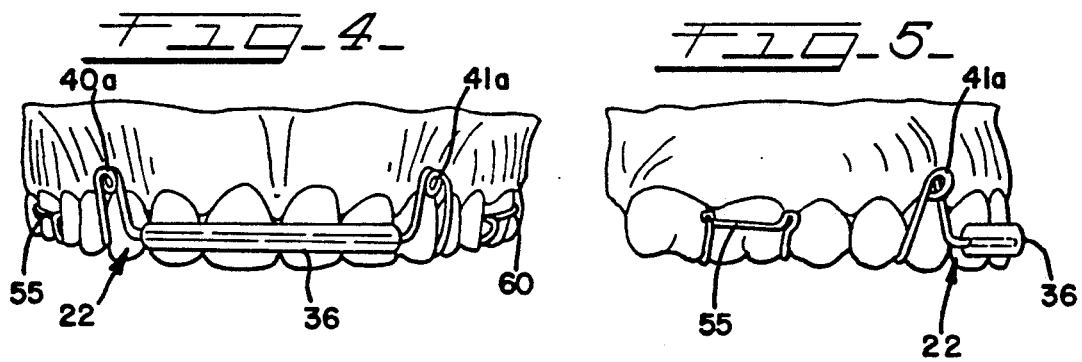

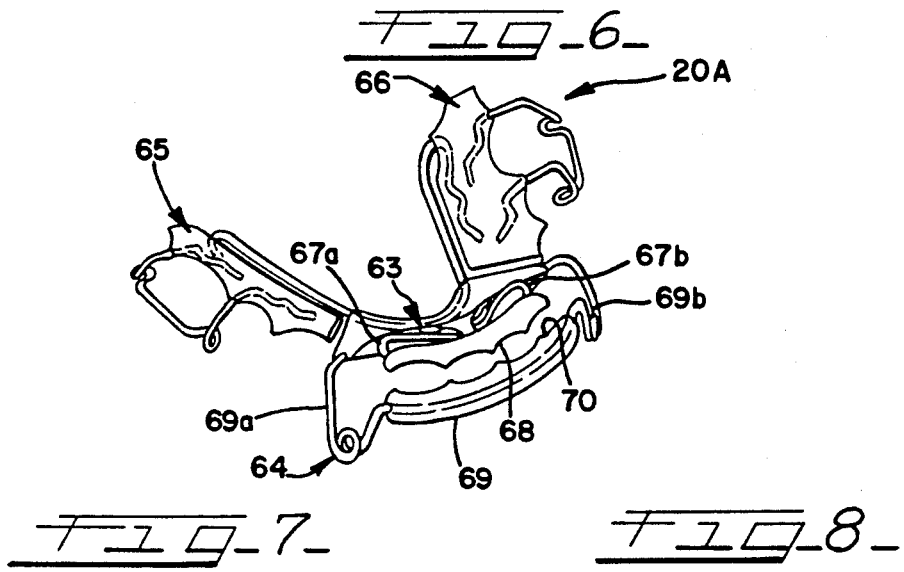
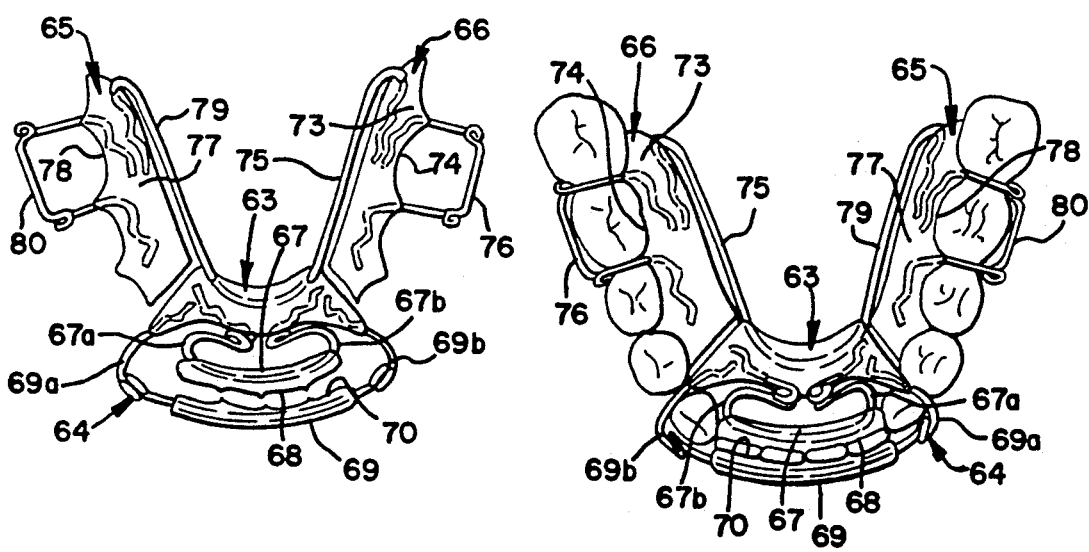
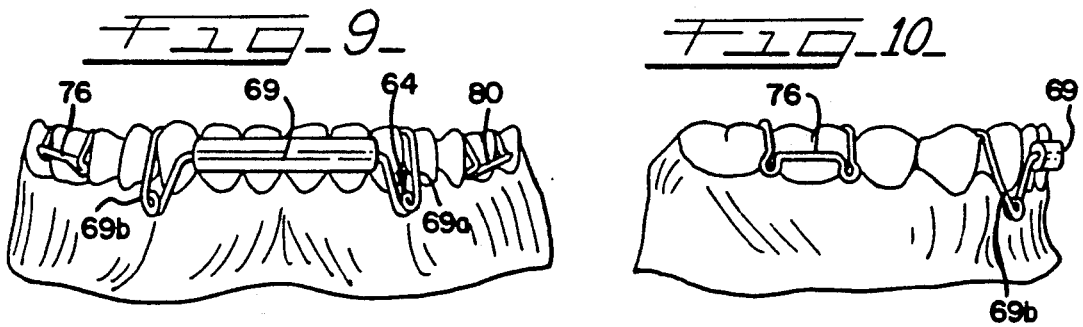

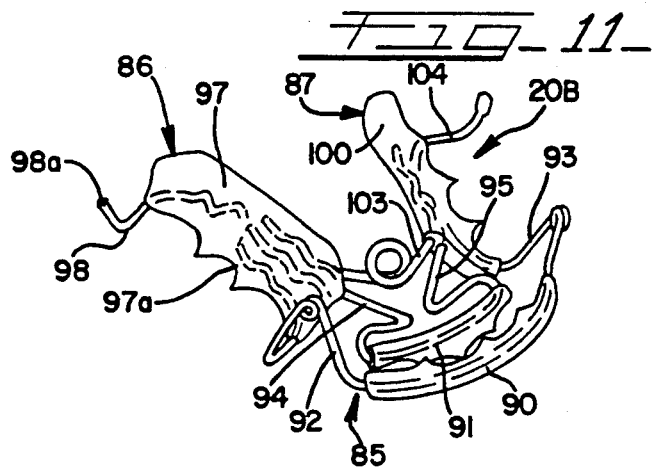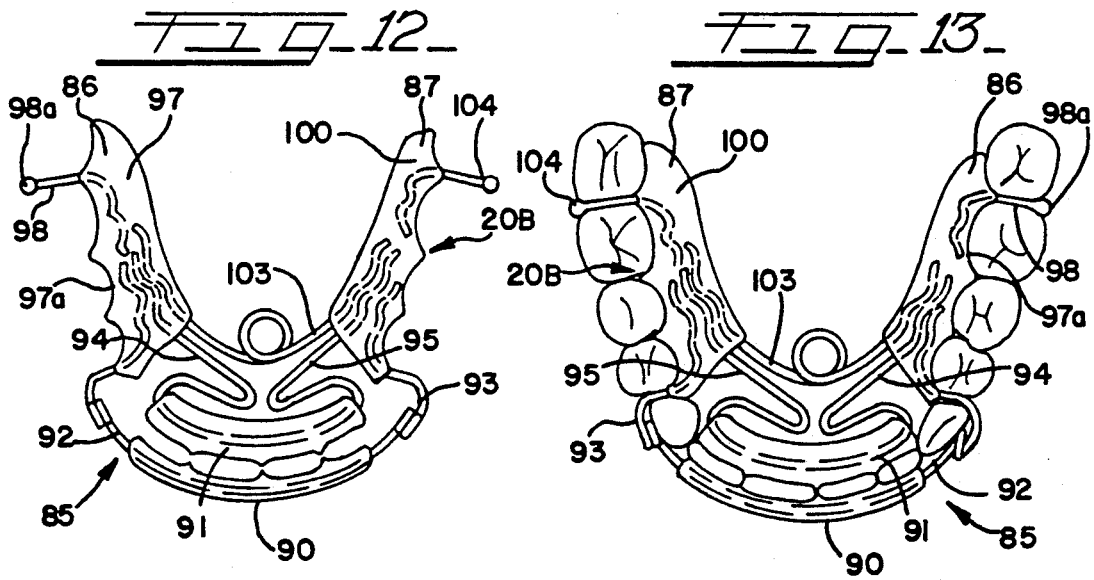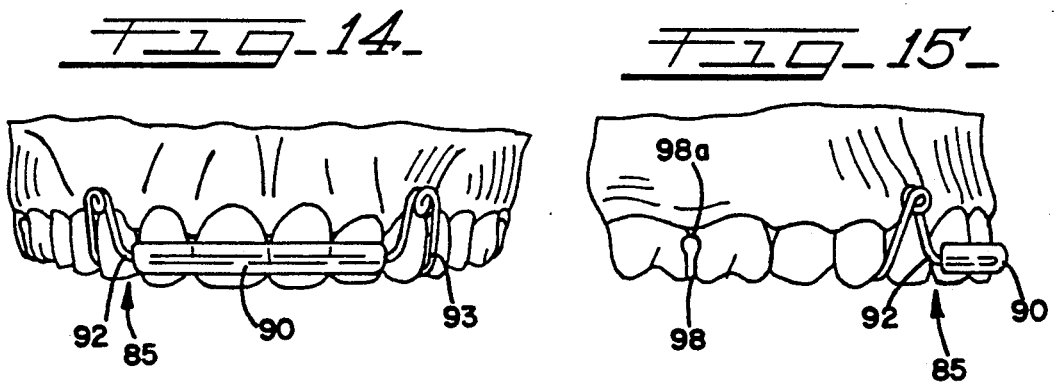

ORTHODONTIC RETAINER

This application is a continuation of application Ser. No. 07/517,370, filed May 1, 1990, now abandoned.

DESCRIPTION

This invention relates in general to a custom prescribed orthodontic appliance for a patient of the type normally referred to as a retainer that is made of acrylic and wire, and more particularly to a retainer having a flexible posterior lingual portion to facilitate fabrication and also to facilitate placement of the appliance in a patient's mouth.

BACKGROUND OF THE INVENTION

Heretofore, retainers have been well known for use in the treatment of orthodontic patients following the removal of fixed appliances for the purpose of retaining the positions of the teeth. Such an appliance is removable and worn by the patient in accordance with instructions given by the orthodontist. While retainers are known for use on anterior teeth only, they are more well known for use on teeth of an entire arch, whether that be upper or lower. A retainer for the entire arch includes an acrylic lingual portion that is custom fit to generally engage the undercuts of the teeth. Wire members are embedded in the acrylic and extend over all or a portion of the teeth to coact with the lingual acrylic portion for retaining the teeth in a desired position. The most well known appliance of this type is called a Hawley retainer. While Hawley retainers have been constructed with several variations as to the wire formations, it is always common to provide the lingual acrylic portion for general fit with the undercuts of the teeth on the lingual side. This fit is more critical for the lower teeth because they lean somewhat inwardly and not as critical for the upper teeth which lean somewhat outwardly.

Successful results from any retainer depend upon the cooperation of the patient, as the patient has the choice of wearing or not wearing the retainer. In the event that a patient fails to wear the retainer for a period of time, difficulty can be experienced in thereafter placing the retainer due to relapse of teeth positions. Heretofore, it has been known to accommodate relapse problems in the anterior by construction of an appliance with resiliently biased portions such as the retainer sold by TP Orthodontics, Inc. and identified as a Spring Aligner Plus. However, no heretofore known retainer has been constructed to accommodate relapse in posterior teeth, and that has caused the patient to choose against wearing the appliance if not worn for a period of time because of the inability to place the appliance in the mouth. It may also cause the orthodontist to reconfigure the lingual acrylic portion of the appliance in order to permit the appliance to be placed and accommodate the posterior relapse.

It has also been well known that during fabrication of an appliance having rigid posterior sections, difficulty is encountered in removing the appliance from the model on which it is made.

SUMMARY OF THE INVENTION

The present invention obviates the heretofore known problems in the fabrication and placement of retainers constructed of acrylic and wire. It will be understood that the term acrylic as used herein is intended to define a material that is rigid in character.

The retainer of the invention is constructed to facilitate its removal from a model on which it is made and to also accommodate relapse in the posterior arch so as to permit the patient to insert and wear the appliance even in the event relapse occurs. More particularly, the appliance of the invention, which is made of acrylic and wire, includes one or more flexible sections in the posterior of the appliance to allow flexing for enhancing the ease of removal of an appliance fabricated on a model and to enhance the ease of placement by a patient where posterior relapse is experienced. Further, the flexible posterior section also lends itself to adjustability by the orthodontist without necessitating the grinding away of the hard acrylic areas that engage the lingual undercuts of the teeth.

It is therefore an object of the present invention to provide a new and improved orthodontic retainer having one or more flexible posterior sections to facilitate fabrication and placement.

Another object of the present invention is to provide a new and improved retainer constructed of acrylic and wire and having at least one of the lingual posterior portions flexibly connected to an anterior lingual portion so as to facilitate fabrication by permitting ease in removal of the appliance from the model on which it is made and to facilitate placement by allowing the posterior section to flex, thereby making it particularly useful where relapse has occurred in the posterior teeth.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a front perspective view of one embodiment of the retainer according to the present invention and fabricated for the upper teeth;

FIG. 2 is a top plan view of the appliance in FIG. 1;

FIG. 3 is a bottom plan view of the appliance of FIG. 1 and illustrating it in mounted position on the upper teeth;

FIG. 4 is a front or labial view of the upper teeth with the appliance of the present invention mounted thereon;

FIG. 5 is a side elevational view of the upper teeth with the appliance of the invention mounted thereon;

FIG. 6 is a top perspective view of another form of appliance according to the present invention for use on lower teeth;

FIG. 7 is a bottom plan view of the retainer of FIG. 6;

FIG. 8 is a top plan view of the retainer of FIG. 6 and illustrating it in mounted relation on the lower teeth;

FIG. 9 is a front or labial view of the lower teeth and showing the retainer of FIG. 6 mounted thereon;

FIG. 10 is a side elevational view of the lower teeth and showing the retainer of FIG. 6 mounted thereon;

FIG. 11 is a top plan view of a modified retainer according to the present invention for use on upper teeth;

FIG. 12 is a top plan view of the retainer of FIG. 11;

FIG. 13 is a bottom plan view of the retainer of FIG. 11 and showing it mounted on the upper teeth;

FIG. 14 is a front or labial elevational view of the upper teeth and showing the appliance of FIG. 11 mounted thereon; and FIG. 15 is a side elevational view of the upper teeth and illustrating the retainer of FIG. 11 mounted thereon.

DESCRIPTION OF THE INVENTION

The retainer of the invention is unique in that the posterior sections or plates which engage the posterior teeth, generally considered to be the bicuspids and molars, are independently sprung or resiliently supported from the anterior section so as to be comfortably worn by a patient having posterior relapse. Additionally, the retainer of the invention, by having the posterior sections or plates flexibly supported from the anterior section, makes it easier to remove from the model after being made, and particularly with respect to a lower retainer. The custom-made retainer of the present invention may be made for the upper teeth or for the lower teeth. When made for the upper teeth, it may include a centrally arranged supporting plate from which is resiliently or flexibly supported the anterior section, as well as the posterior sections. Alternatively, the anterior and posterior sections may be directly connected to be flexibly related to each other.

Referring now to the embodiment of FIGS. 1 to 5, an orthodontic retainer according to the invention and generally designated by the numeral 20 is illustrated and which has been custom fabricated for a patient for the upper arch or teeth. This retainer includes a main and centrally disposed plate or section 21 having flexibly supported therefrom an anterior section 22 and a pair of posterior sections 23 and 24. The main supporting or base plate 21 is formed to fit up against the anterior portion of the palate, while the anterior section 22 is formed to engage and retain the six anterior teeth, including the centrals, laterals, and canines. The posterior sections 23 and 24 opposing each other are formed to fit against the opposite edge portions of the palate and lingually engage the undercuts of the upper posterior teeth, including the bicuspids and molars, as seen particularly in FIG. 3.

The main palatal plate 21 is somewhat triangular in shape and is formed of hard acrylic of a conventionally known type. Extending forward or labially from the main plate 21 is the anterior section 22 which includes a rigid gingival plate 30 having a lingual custom-formed edge 31 adapted to precisely fit the lingual surfaces of the centrals and laterals, as seen particularly in FIG. 3. Plate 30 is flexibly connected to the main plate 21 by means of flexible wire connectors 33 and 34, each of which includes a coil section 33a and 34a. Thus, the plate 30 is flexibly supported from the main plate 21. A labial plate 36 is also included in the anterior section which is in opposing relation to the lingual plate 30 and which includes the custom-formed tooth-engaging edge 37 that labially engages the labial surfaces of the four front teeth, including the centrals and the laterals, as particularly seen in FIGS. 3, 4 and 5. Labial plate 36 is flexibly supported from the main plate 21 by means of wire connectors 40 and 41 which include coils 40a and 41a. Thus, even the labial plate 36 is independently suspended from the main plate 21 even though it is arranged to coact with the lingual plate 30. It will be understood that the labial plate 36 is also of rigid acrylic like the gingival plate 30 and the main plate 21.

The right posterior section 23 includes a rigid gingival plate 45 which is flexibly supported from the main plate 21 by a wire spring arm 46. Similarly, the posterior section 24 includes a rigid gingival plate 49 that is flexibly supported from the main plate 21 by means of spring arm 50. Thus, both posterior rigid gingival plates 45 and 49 are flexibly supported and in independent fashion from the main plate 21 and particularly independent of the suspension of the anterior section.

The right rigid gingival plate 45 includes a custom-contoured lingual tooth-engaging edge 53 which lingually engages the upper right posterior teeth to assist in holding the retainer in place. An Adam's clasp 55 is cantileverly supported from the upper right rigid plate 45 to clasp over the first molar, as shown in FIGS. 3, 4 and 5.

Similarly, the left rigid gingival plate 49 includes a custom-contoured edge 58 for matingly engaging the lingual undercuts of the left posterior teeth, as seen in FIG. 3. Further, to assist in holding the retainer in place, an Adam's clasp 60 is cantileverly carried by the rigid gingival plate 49 and for purposes of clasping over the first molar.

The anterior section, in addition to receiving the four anterior teeth, also receives for retention the canines in the area between the plates 30, 36 and the plate 21, as particularly seen in FIG. 3.

It will now be seen that the embodiment of FIGS. 1 to 5 includes a main plate 21, two posterior rigid gingival plates 45 and 49, two anterior plates 30 and 36, together with sufficient flexible wire to interconnect the plates together. The wire is in each case embedded in the plates so that the entire appliance is interconnected together. It can now be appreciated that should there be any posterior relapse of the posterior teeth the appliance, by virtue of its flexibility in the posterior area can be comfortably placed and worn by a patient and which will allow the plates to function independent of one another and to allow the retainer to be more easily removed from the model after it is molded and to allow the retainer to be more comfortably worn if there is posterior teeth relapse.

Reference is now made to the embodiment of FIGS. 6 to 10, which illustrate a retainer of the invention, generally designated by the numeral 20A, which would be custom made for a patient and for use on the lower arch or the lower teeth. This retainer is made in a similar fashion to the retainer of FIGS. 1 to 5 with the exception that it will provide retention for the lower teeth. The retainer 20A includes a main support plate 63 of acrylic and from which the anterior section 64 is flexibly supported as well as the posterior sections 65 and 66. The main support plate 63 fits against the bottom of the mouth beneath the tongue in a custom fashion and has anchored therein portions of wires that support the anterior section 64 and posterior sections 65 and 66.

The anterior section 64, like the anterior section 22 of the embodiment of FIGS. 1 to 5, includes a lingual plate 67 of acrylic having a wire embedded therein with end portions forming spring support arms 67a and 67b which have ends terminating in the main plate 63 and which are of the same type as the wire connectors or arms 33 and 34 of the retainer 20. A labially facing tooth-engaging edge 68 conforms to the lingual surfaces of the four front teeth, as seen in FIG. 8. Similar to the first embodiment, a labial plate 69 of acrylic is spring supported by spring arms 69a and 69b to the main support plate 63 and includes a lingually facing edge 70 custom molded to engage the labial surfaces of the four front teeth, as shown in FIG. 8. Thus, the plates 67 and 69 coact with each other to engage and retain in position the four front teeth. Further, the canines are received and retained in position by the anterior section 64 in the same manner as the canines are retained with respect to the first embodiment. The plates 67 and 69, as seen particularly in FIGS. 8, 9 and 10, are opposed to one another and generally engage the intermediate portions of the exposed areas of the lower teeth, as illustrated.

The posterior section 66 functions to retain the posterior teeth at the right side of the mouth, while the posterior section 65 functions to retain the posterior teeth at the left side of the mouth. Section 66 includes a rigid gingival acrylic plate 73 having a tooth-engaging edge 74 which is custom-fitted to the lingual undercut surfaces of the four posterior teeth and which is flexibly supported from the main plate 63 by a spring arm 75 in the form of a flexible wire which has one end embedded at the distal end of the plate 73 and the other end portion embedded in the main support plate 63. Additionally, an Adam's clasp 76 is supported by the rigid plate 73 for extending over the first molar and assisting in clasping the retainer in place.

Similarly, the posterior section 65 includes a rigid custom-formed plate 77 having a form-fitting tooth-engaging edge 78 which fits against the lingual undercut area of the left posterior teeth. Plate 77 is flexibly connected to the main plate 63 by a spring arm 79, one end of which is embedded in and anchored at the distal portion of the main plate 77 and the other end of which is embedded in and anchored to the main plate 63. An Adam's clasp 80 is carried by the rigid plate 77 for engaging and clasping the first molar on the left side in a similar fashion as the Adam's clasp 76. For purposes of construction, the spring arms 75 and 79 may be made from the same length of wire having its intermediate portion anchored in the main plate 63. This wire section is generally U-shaped with the central portion carried by the main support plate 63. Placement of the retainer on the lower arch or lower teeth is illustrated, as seen in FIGS. 8, 9 and 10. Again, should there be any relapse in the posterior teeth, the flexible posterior sections will allow comfortable placement of the retainer within the mouth of the patient and also then function to move the teeth back to the position to be retained by the retainer.

The retainer 20A will function in substantially the same manner as the retainer 20, it being understood that the retainer 20A is custom made for the lower arch or lower teeth.

Referring now to the embodiment of FIGS. 11 to 15, a retainer 20B according to the invention differs from the retainers 20 and 20A in that while the anterior and posterior sections are interconnected so as to be independent of one another and thereby flexibly interconnected, the interconnections are accomplished entirely by the use of flexible wires or springs, and the use of a main support plate is eliminated. Retainer 20B is custom made for use on the upper arch or teeth and includes generally an anterior section 85, a right posterior section 86 and a left posterior section 87. The anterior section is custom-fitted for retaining the positions of the six anterior teeth and the posterior sections are custom-fitted for retaining the positions of the eight posterior teeth, four on each side.

The anterior section 85 includes first and second rigid gingival plates 90 and 91 of acrylic, each having tooth-engaging edges and disposed opposite one another to coact and respectively engage the labial and lingual surfaces of the four anterior teeth. Opposed spring support arms 92 and 93, having their distal ends embedded in and anchored in the posterior sections, support the first rigid gingival plate 90. Internally positioned spring arms 94 and 95 have their distal ends connected to the posterior sections and flexibly support the second rigid gingival plate 91 of the anterior section.

The right posterior section 86 includes a rigid gingival lingual plate 97 which includes a custom-formed tooth-engaging edge 97a for engagement at the lingual undercut areas of the right posterior teeth. Additionally, a one-armed clasp 98 extends from the plate 97 for engagement over the upper teeth and which includes a balled end 98a for engaging in the buccal embrasure between the two rear molars. Thus, clasp 98 assists in holding the retainer in place. Similarly, the left posterior section 87 includes a rigid lingual gingival plate 100 which anchors spring arms 93 and 95 of the anterior section 85 and which is flexibly interconnected with the rigid plate 97 on the right posterior section by a spring arm 103 having one or more helical loops. A one-arm ball clasp 104 extends from the rigid plate 100 to engage in the buccal embrasure of the two left molars to assist in holding the retainer in place on the teeth.

Accordingly, the posterior sections 86 and 87 are flexibly interconnected and the anterior section 85 is flexibly interconnected to the rear posterior sections so that each of the posterior sections is independently suspended from the anterior section and each other, and likewise the anterior section is independently suspended from each of the posterior sections. Therefore, retainer 20B will function in a similar manner to retainers 20 and 20A and where posterior relapse can be easily accommodated. Further, removal of a retainer after being molded on a model can be accomplished by virtue of the ability of the posterior sections to easily give relative to each other and relative to the anterior section.

It will be understood that modifications and variations may be effected without departing from the scope of the novel concepts of the present invention, but it is understood that this application is to be limited only by the scope of the appended claims.

The invention is hereby claimed as follows:

1. A custom-made orthodontic retainer for an arch of a patient comprising, an anterior section for engaging the anterior teeth, and a posterior section for engaging the posterior teeth, said anterior section including a rigid base plate and a rigid gingival plate for lingually engaging anterior teeth; said posterior section including a pair of rigid gingival plates for lingually engaging the posterior teeth one at each side of the arch, flexible wire anchored in the plates and interconnecting the plates, and at least one of the posterior rigid gingival plates being flexibly connected by wire to the base plate such that the flexibly connected posterior plate facilitates removal of the appliance from the model on which it is fabricated and facilitates placement on the teeth by the patient.

2. The retainer of claim 1, wherein both posterior rigid gingival plates are flexibly connected by wire to the base plate.

3. The retainer of claim 1, wherein the sections are formed for the lower arch.

4. The retainer of claim 1, wherein the sections are formed for the upper arch.

5. The retainer of claim 1, wherein the anterior section further includes a rigid plate labially engaging anterior teeth.

6. The retainer of claim 1, wherein the rigid plates are acrylic.

7. A custom-made orthodontic retainer for an arch of a patient comprising, an anterior section for engaging the anterior teeth, and a posterior section for engaging the posterior teeth, said posterior section including a pair of rigid gingival plates for lingually engaging the posterior teeth one at each side of the arch, a flexible wire anchored in and intermediate the posterior gingival plates for interconnecting the plates such that the posterior plates are flexibly connected together to facilitate removal of the appliance from the model on which they are fabricated and facilitate placement on the teeth by the patient, said anterior section including a rigid gingival plate for lingually engaging anterior teeth, and a pair of flexible wires one at each end of the anterior gingival plate for interconnecting the anterior gingival plate to the posterior gingival plates.

8. The retainer of claim 7, wherein one of the wires of the anterior gingival plate extends to one of the posterior gingival plates and the other wire of the anterior gingival plate extends to the other of the posterior gingival plates.

9. The retainer of claim 8, wherein the wire intermediate the posterior gingival plates includes a helix to enhance flexibility between the posterior gingival plates.

10. The retainer of claim 8, wherein the wire intermediate the posterior gingival plates includes a spring element to enhance flexibility between the posterior gingival plates.

11. A custom-made orthodontic retainer for an arch of a patient comprising, an anterior section for engaging the anterior teeth, and a posterior section for engaging the posterior teeth, said posterior section including a pair of rigid gingival plates for lingually engaging the posterior teeth one at each side of the arch, a flexible wire anchored in and intermediate the mesial ends of the posterior gingival plates for interconnecting the plates such that the posterior plates are flexibly connected together to facilitate removal of the appliance from the model on which they are fabricated and facilitate placement on and removal from the teeth by the patient, said intermediate flexible wire including a helix to enhance flexibility between the posterior plates, said anterior section including a rigid gingival plate for lingually engaging anterior teeth, and a pair of flexible wires one extending from each end of the anterior gingival plate for interconnecting the anterior gingival plate to each of the posterior gingival plates, one of the wires of the anterior gingival plate extending to and connected to one of the posterior gingival plates and the other wire of the anterior gingival plate extending to and connected to the other of the posterior gingival plates.

12. A custom-made orthodontic retainer for an arch of a patient comprising, an anterior section for engaging the anterior teeth, and a posterior section for engaging the posterior teeth, said posterior section including a pair of rigid gingival plates for lingually engaging the posterior teeth one at each side of the arch, a flexible wire anchored in and intermediate the mesial ends of the posterior gingival plates for interconnecting the plates such that the posterior plates are flexibly connected together to facilitate removal of the appliance from the model on which they are fabricated and facilitate placement on and removal from the teeth by the patient, said intermediate flexible wire including a looped portion to enhance flexibility between the posterior plates, said anterior section including a rigid gingival plate for lingually engaging anterior teeth, and a pair of wire extremities one at each end of the anterior gingival plate for interconnecting the anterior gingival plate to the posterior gingival plates, one of the wire extremities of the anterior gingival plate extending to one of the posterior gingival plates and the other wire extremity of the anterior gingival plate extending to the other of the posterior gingival plates.

* * * * *